United States Patent [19]

Roy et al.

[11] Patent Number: 5,290,945
[45] Date of Patent: Mar. 1, 1994

[54] PROCESS FOR PREPARING BISIMIDE PRODUCTS

[75] Inventors: Ranjit K. Roy; Ali M. Dadgar; Donald O. Hutchinson; Keith G. Anderson, all of Baton Rouge, La.

[73] Assignee: Ethyl Corporation, Richmond, Va.

[21] Appl. No.: 925,446

[22] Filed: Aug. 11, 1992

Related U.S. Application Data

[63] Continuation of Ser. No. 832,947, Feb. 10, 1992, abandoned, which is a continuation of Ser. No. 497,668, Mar. 23, 1990, abandoned.

[51] Int. Cl.$^5$ ............................................. C07D 403/06
[52] U.S. Cl. ................................................ 548/462
[58] Field of Search ........................................ 548/462

[56] References Cited

U.S. PATENT DOCUMENTS

| | | | |
|---|---|---|---|
| 3,868,388 | 2/1975 | Dotson, Jr. et al. | 260/326 N |
| 3,915,930 | 10/1975 | Dotson, Jr. et al. | 260/45.8 N |
| 3,966,726 | 6/1976 | Toth et al. | 260/249.8 |
| 4,092,345 | 5/1978 | Wolford et al. | 260/501.16 |
| 4,125,535 | 11/1978 | Wolford | 260/326 N |
| 4,374,220 | 2/1983 | Sonnenberg | 524/94 |
| 4,535,170 | 8/1985 | Sonnenberg | 548/462 |
| 4,581,396 | 4/1986 | Sonnenberg | 524/87 |
| 4,990,626 | 2/1991 | Hutchinson et al. | 548/462 |
| 4,997,953 | 3/1991 | McKenna | 548/461 |

FOREIGN PATENT DOCUMENTS

| | | |
|---|---|---|
| 0023420 | 7/1980 | European Pat. Off. . |
| 0195402A3 | 9/1986 | European Pat. Off. . |
| 1815404 | 6/1970 | Fed. Rep. of Germany . |
| 1951632 | 5/1971 | Fed. Rep. of Germany . |
| 2926638 | 1/1981 | Fed. Rep. of Germany . |

Primary Examiner—Mary C. Lee
Assistant Examiner—Jacqueline Haley
Attorney, Agent, or Firm—Edgar E. Spielman, Jr.

[57] ABSTRACT

This invention relates to a process for preparing a white bisimide product which principally contains N,N'-alkylene-bis(tetrabromophthalimide) or N,N'-bis(tetrabromophthalimide). The process features: providing, in a reaction vessel, a solution containing tetrabromophthalic anhydride and a solvent which contains at least about 15 weight percent of a mono-, di- or tri- carboxylic acid having a dissociation constant not higher than $1.0 \times 10^{-3}$ at 25° C.; forming a reaction mass by adding to the solution a diamine or a diamine salt formed by the partial or total diamine neutralization of a mono-, di- or tri- carboxylic acid having a dissociation constant not higher than $1.0 \times 10^{-3}$ at 25° C., such formation of the reaction mass resulting in the production of a bisimide precipitate which becomes a constituent of the reaction mass; during the formation of the reaction mass, (i) retaining, in the reaction mass, at least a portion of the water produced during such formation, (ii) maintaining a substantially constant pressure in the reaction vessel, and (iii) not allowing the temperature of the reaction mass to reach a temperature below about 135° C.; terminating the addition of the diamine or diamine salt when the molar ratio of the tetrabromophthalic anhydride initially present in the solution to the diamine or diamine salt added is from about 1.9:1 to about 2.1:1; and recovering, as the bisimide product, the bisimide precipitate.

8 Claims, No Drawings

PROCESS FOR PREPARING BISIMIDE PRODUCTS

This application is a continuation of Ser. No. 07/832,947, filed Feb. 10, 1992, now abandoned, which is a continuation of Ser. No. 07/497,668, filed Mar. 23, 1990, now abandoned.

BACKGROUND OF THE INVENTION

This invention relates to an improved process for preparing a white halogenated bisimide product having good filterability and a low Yellowness Index (Y.I.) as measured by ASTM 1313.

As is taught in U.S. Pat. No. 4,374,220, there are a multitude of halogenated bisimides which are effective as flame retardants in formulation with macromolecular flammable materials, e.g. polymers. These formulations are useful in making articles such as wire insulation and electronic housings. Of the halogenated bisimides, the N,N'-alkylene-bis(tetrabromophthalimide)s and the N,N'-bis(tetrabromophthalimide)s are especially commercially significant.

A presently used commercial route for producing a product which principally contains N,N'-alkylene-bis(-tetrabromophthalimide) comprises reacting tetrabromophthalic anhydride with a diaminoalkane in the presence of water and an alkanoic acid to yield a reaction mass containing the intermediate, N,N'-alkylene diammonium-bis(tetrabromophthalate). The reaction mass is then heated to about 225° C. for a period of about 2 hours to convert the intermediate to N,N'-alkylene-bis(tetrabromophthalimide) which is the principal constituent of the product recovered from the reaction mass. This product is particularly useful as it has good thermal stability and resistance to UV degradation. However, the product has a yellow color which argues against its presence in compositions used for forming white articles. Also, the intensity of the yellow color can vary between product batches, which color variance, if severe, can make it difficult for the article manufacturer to maintain consistency in the color of the articles produced. The yellow color is believed to be due to impurities formed during the conversion of the N,N'-alkylene diammonium-bis(tetrabromophthalate) intermediate to the corresponding bisimide product.

THE INVENTION

This invention relates to a process for preparing a very white bisimide product, which product principally contains N,N'-alkylene-bis(tetrabromophthalimide) or N,N'-bis(tetrabromophthalimide). The process features: providing, in a reaction vessel, a solution containing tetrabromophthalic anhydride and a solvent, which solvent contains at least about 15 weight percent of a mono-, di- or tri- carboxylic acid having a dissociation constant not higher than $1.0 \times 10^{-3}$ at 25° C.; forming a reaction mass by adding to the solution a diamine or a diamine salt formed by the partial or total diamine neutralization of a mono-, di- or tri- carboxylic acid having a dissociation constant not higher than $1.0 \times 10^{-3}$ at 25° C., such formation of the reaction mass resulting in the production of a bisimide precipitate which becomes a constituent of the reaction mass; during the formation of the reaction mass, (i) retaining in the reaction mass at least a portion of the water produced during such formation, (ii) maintaining a substantially constant pressure in the reaction vessel, and (iii) not allowing the reaction mass to reach a temperature below about 135° C.; terminating the addition of the diamine or diamine salt when the molar ratio of the tetrabromophthalic anhydride initially present in the solution to said diamine or diamine salt added is within the range of from about 1.9:1 to about 2.1:1; and recovering, as the bisimide product, the bisimide precipitate.

DETAILED DESCRIPTION OF THE INVENTION

For the purposes of this disclosure, the N,N'-alkylene-bis(tetrabromophthalimide) and the N,N'-bis(tetrabromophthalimide) will hereinafter be referred to collectively as bisimide and are represented by the formula,

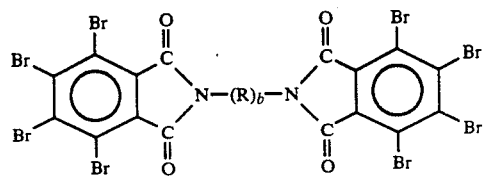

wherein R is an alkylene radical containing 1 to 6 carbon atoms and b is 1 or 0. R can be a branched or be a straight chain radical. R is preferably methylene, ($-CH_2-$), or ethylene, ($-CH_2-CH_2-$). When b is 0, the bonding between the two cyclic groups is via a N—N bond.

The bisimide precipitate and product are predominantly comprised of bisimide. Impurities which may be present are solvent, tetrabromophthalic anhydride, tetrabromophthalimide, N,N'-alkylene-bis(propionamide), N,N'-bis(propionamide) and N-(ethylene-2-tetrabromophthalimido)propionamide. Generally, the bisimide will constitute at least 98 weight percent of the bisimide product.

The reactions involved in the process of this invention can be represented by the following:

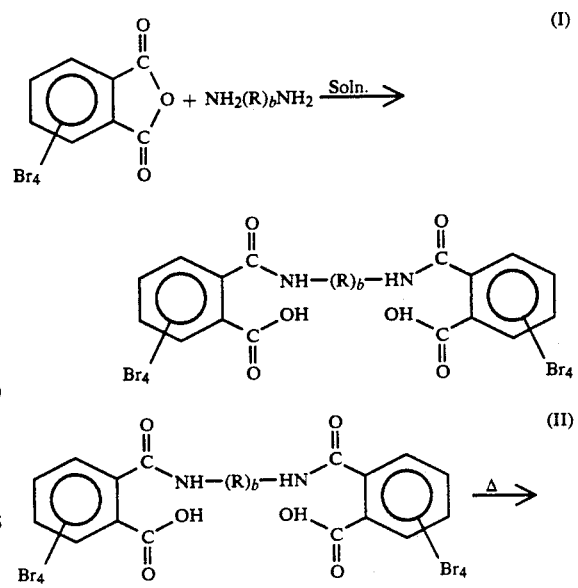

-continued

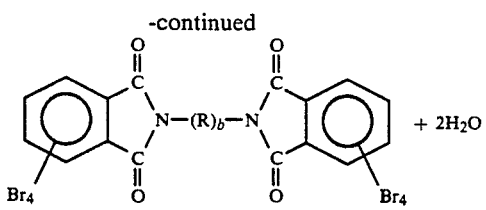 + 2H₂O

As can be appreciated from the foregoing, a considerable amount of water is produced during the cyclization of the amic acid intermediate.

The diamine that is used in the process of this invention can be represented by the formula: $H_2N\text{-}(R)_b\text{-}NH_2$ wherein R and b are as defined above. For example, the diamine can be 1,1-diaminomethane, 1,2-diaminoethane, 1,2-diaminopropane, 1,3-diaminopropane, 1,4-diaminobutane, 1,5-diaminopentane, 1,6-diaminohexane, hydrazine, etc. The diamine reactant can also be a mixture of diamines, however, the final product obtained will not be a single species but rather will be a mixture of species as determined by the diamine mixture used. Preferred diamines are hydrazine and 1,2-diaminoethane as they yield particularly useful white flame retardant products. The diamine can be added neat or in solution with a solvent, e.g. o-, m-, p- xylene or a mixture thereof. Technical or commercial grade xylene can be used, such xylene being comprised of a mixture predominate in o-, m- and p- xylenes, and to a lesser extent, ethyl benzene.

The partially or totally diamine neutralized mono-, di- or tri- carboxylic acid salts which can be used in the practice of this invention will, hereinafter, simply be referred to as diamine salts. The carboxylic acid constituent of the diamine salt is derived from an acid having a dissociation constant not greater than about $1.0 \times 10^{-3}$ at 25° C. The preferred derivative acids are alkanoic and aralkanoic carboxylic acids containing 2 to 12 carbon atoms and mixtures thereof. Most preferred of these acids are alkanoic acids having a dissociation constant less than $1.8 \times 10^{-5}$ at 25° C. and containing 2 to 6 carbon atoms. Exemplary of suitable derivative carboxylic acids are: acetic acid, propionic acid, isobutyric acid, valeric acid, hexanoic acid, toluic acid, acrylic acid, benzoic acid, bromobenzoic acid, phenylacetic acid, p-methylphenylacetic acid, alpha phenylpropionic acid, succinic acid, glutaric acid, adipic acid, and mixtures thereof. Propionic acid is preferred. The cationic diamine constituent of the diamine salt can be derived from the $H_2N\text{-}(R)_b\text{-}NH_2$ diamines and the mixtures thereof which are discussed above. Preferred salts are the hydrazine and diaminoethane salts. Especially preferred are the hydrazine and diamino ethane salts of propionic acid.

It is also possible to use a mixture of the abovedescribed diamines and diamine salts in the practice of the process of this invention. For simplicity, such mixtures are to be taken as being included in the phrase "diamine or diamine salts" as hereinafter used.

The solvent used in the process of this invention is one in which the tetrabromophthalic anhydride is soluble and in which the bisimide precipitate is substantially insoluble. Further, the solvent should not adversely affect the yield, the color or the physical characteristics of the bisimide product.

It is preferred that the solvent chosen be one which, when in mixture with the water formed during the formation of the reaction mass, will yield a reaction mass which is at its boiling point under the reaction temperature and pressure. By having a boiling condition, control of the reaction temperature is facilitated in cooperation with the water removal and pressure control features hereinafter described. It is particularly useful to recover the solvent by refluxing it back to the reaction mass.

The solvent can be comprised of a single constituent or a plurality of constituents. A necessary constituent is a mono-, di- or tri- carboxylic acid having a dissociation constant not higher than $1.0 \times 10^{-3}$ at 25° C. Exemplary of suitable carboxylic acids are: acetic acid, propionic acid, isobutyric acid, valeric acid, hexanoic acid, toluic acid, acrylic acid, benzoic acid, bromobenzoic phenylacetic acid, p-methylphenylacetic acid, alphaphenylpropionic acid, succinic acid, glutaric acid, adipic acid, and mixtures thereof. Preferred carboxylic acids are the alkanoic and the aralkanoic carboxylic acids containing 2 to 12 carbon atoms, with alkanoic acids having a dissociation constant of less than $1.8 \times 10^{-5}$ at 25° C. and containing 2 to 6 carbon atoms being more preferred. A most preferred acid is propionic acid. Quantitatively, the mono-, di- or tri- carboxylic acid is present in the solvent in an amount in excess of about 15 weight percent, based upon the total weight of the solvent. Preferred amounts are within the range of from about 25 weight percent to about 100 weight percent. Most preferred amounts are 30 weight percent and 100 weight percent.

An optional solvent constituent is an aromatic hydrocarbon or an aromatic halohydrocarbon which has a boiling point above about 80° C. at atmospheric pressure. Examples of suitable aromatic compounds are: benzene; o-, m-, p- xylene, and mixtures of such xylenes; mesitylene; cumene; pseudocumene; o-, m-, p- diethylbenzene, and mixtures of such diethylbenzenes; ethylbenzene; o-, m-, p- dichlorobenzenes, and mixtures of such dichlorobenzenes; chlorobenzene; and mixtures of the foregoing. Preferred are o-, m-, p- xylene and mixtures thereof. Technical or commercial grades of xylene are also preferred, which grades can contain significant quantities of ethylbenzene.

The solvent can contain other constituents which may or may not contribute to the solvent function provided that such constituents do not unduly interfere with the process or with the quality of the bisimide product formed.

One preferred solvent is comprised essentially of propionic acid, say about 99+ weight percent propionic acid. Other preferred solvents are those which contain from about 85 weight percent to about 70 weight percent o-, m- or p- xylene or mixtures thereof, and from about 15 weight percent to about 30 weight percent propionic acid, all based upon the total weight of the solvent.

The tetrabromophthalic anhydride/solvent solution provided to the reaction vessel can be formed in the reaction vessel or can be formed exteriorly of the reaction vessel and then added thereto.

The addition of the diamine or diamine salt to the tetrabromophthalic anhydride/solvent solution should occur at a temperature within the range of from about 140° C. to about 200° C., and preferably within the range of from about 150° C. to about 180° C. Temperatures in excess of 200° C. should not be used as undesirable reactions between the solvent and the bisimide are a possibility. During the addition, water will be produced in accordance with reaction (II). This water will become part of the reaction mass and, since the addition occurs under constant pressure, there will be a drop in the reaction mass temperature. This drop is not deleterious provided that it does not result in the reaction mass temperature going below about 135° C., and preferably 140° C. In most cases, this lower temperature boundary will be crossed if some of the water in the reaction mass is not removed therefrom. This is not to say that all of the water should be removed, as it is believed that some water must be retained in the reaction mass during the addition, and, thus, water removal is preferably restricted to that extent which is needed to keep the reaction mass at the temperature above 135° C. which is selected. The water that is removed, can be removed by means of a conventional condenser and two phase separator train in which the solvent is refluxed back to the reaction vessel minus that amount of water selected for removal. It is preferred that at least about 25 percent of the water produced be retained in the reaction mass at least until the mass is completely formed. Preferred amounts of retained water are within the range of from about 25 to about 90 percent.

Not only can water removal be effected by refluxing, condensing and phase separation, but it also can be accomplished by chemical or mechanical techniques. Chemical techniques for removing water from the reaction mass include the addition of a dehydrating agent to the reaction mass. Exemplary dehydrating agents are propionic anhydride, acetic anhydride, phosphorous pentoxide and the like. Mechanical techniques include the use of molecular sieves and the like.

The reaction vessel pressure during the diamine or diamine salt addition is substantially constant and is suitably within the range of from about 5 psig to about 40 psig. It is preferred to select a pressure which will provide reflux of the initial reactor contents, i.e. the solvent and tetrabromophthalic anhydride, at the chosen initial temperature. With the pressure so chosen to provide refluxing conditions, temperature control of the reactor contents is made easier. For example, a pressure of about 10 psig to about 30 psig would be suitable for an initial temperature of 150° C. to 180° C. and for a solvent comprised of 70 to 85 weight percent o-, m- or p- xylene or mixtures thereof and 15 to 30 weight percent propionic acid. The foregoing weight percents are based upon the total weight of the solvent.

It is theorized, though this invention is not limited by such a theory, that the retention of water combined with either the fall in reaction mass temperature, the maintenance of substantially constant pressure, or both of these result in the production of bisimide product having a superior white color.

The quantitative relationship between the tetrabromophthalic anhydride and the diamine or diamine salt used should be substantially stoichiometric, i.e. a molar ratio of anhydride to diamine or diamine salt within the range of from about 1.9:1 to about 2 1:1. A preferred ratio is within the range of from about 2:1 0 percent molar excess anhydride) to about 2.07:1 (3.5 percent molar excess anhydride) as such ratios contribute to producing product with good color. Molar ratios in which there is less than about 2.0 moles of anhydride per mole of diamine or diamine salt produces product with a lower color quality.

The rate of diamine or diamine salt addition is believed to be a contributing factor to particle size and product color. Slow diamine or diamine salt addition rates yield a product having a larger particle size and a higher yellowness index value. Thus, to obtain best product color, the diamine is added as quickly as is practical without causing the process temperature to get out of control. On the other hand, to obtain larger particle sizes the addition should be over a long period of time. Even though the sphericity of the particles is the largest factor in determining filterability, very small particle size does contribute to lowering filterability qualities. Thus, the practitioner of this invention will have to balance between the best product color and filterability in choosing the diamine or diamine salt addition rates. This choice is made based upon empirical study considering the requirements of the final product, filtering equipment available and the process economics desired.

To enhance the filterability of the bisimide precipitates produced by the processes of this invention, it is advantageous to cook the reaction mass after the diamine or diamine salt addition. At initial formation, the bisimide precipitate will generally have a plate-like form, which form is not suitable for obtainment of short filtration times. It has been found that if the reaction mass is cooked subsequent to the diamine or diamine salt addition step, the sphericity of the precipitate is enhanced which sphericity creates voids in the precipitate mass and, thus, gives the precipitate mass enhanced filterability. Sphericity is defined as the ratio of the surface area of a sphere which has the same volume as the particle being measured to the surface area of the particle.

The cooking temperature can be within the range of from about 140° C. to about 200° C. Temperatures much above 200° C., should be avoided so as to not promote reaction between the solvent and the bisimide precipitate. Preferred cooking temperatures are within the range of from about 150° C. to about 170° C. Most highly preferred cooking temperatures are within the range of from about 160° C. to about 170° C.

The cooking period is that period of time which effects the increase in sphericity sought. It has been found that the higher cooking temperatures, e.g. 160° C. to 170° C. require substantially shorter cooking times than do the lower temperatures, e.g. 140° C. to 150° C. Also, it is possible, with the higher temperatures, to obtain a bisimide product having a lower filtration time than that which is obtainable with the lower temperatures. It has been found that for any given cooking temperature there is a cooking period beyond which further cooking is of little consequence in decreasing filtration times. Thus, the practitioner of this invention would select a desired filtration time for the bisimide precipitate and then determine by trial and error the cooking period needed to obtain that filtration time, it being realized that there is a bottom limit to the filtration time achievable. Generally, the cooking period, at 160° C. to 170° C., needed for the lowest filtration times is within the range of 2 hours to about 6 hours.

It is to be understood that the cooking step can be performed on the reaction mass immediately after the diamine or diamine salt addition is finished or can be performed on the bisimide precipitate which has been recovered from the reaction mass after the diamine or diamine salt addition. The former is preferred. When the latter procedure is used, a slurry containing a liquid and the bisimide precipitate must be formed, which slurry is then subjected to the cooking conditions.

During the cooking period the reaction mass is preferably kept at reflux. Since most of the water formed by cyclization will have formed before achievement of the major portion of the cooking period, the practitioner need only adjust the cooking temperature and pressure to obtain refluxing conditions. It is preferred to use the same pressure that was used during the diamine or diamine salt addition. However, other pressures can be used.

After cooking, the bisimide precipitate obtained is recovered, as the bisimide product, from the reaction mass by any conventional means, e.g. filtration, centrifugation, etc. For commercial production, recovery of the product by use of a rotary drum vacuum filter is believed to be preferred. It has also been found that the recovery rate can be increased, in some cases, by effecting the recovery at an elevated temperature, say from about 65° C. to about 135° C. However, temperatures in excess of 85° C. are generally not preferred when stainless steel equipment is used due to unacceptable corrosion rates.

After recovery, the bisimide product, whether exposed to the cooking step or not, is preferably washed to reduce the content of any non-bisimide impurities which are present. Washing can be effected by using any wash solvent which is capable of solubilizing to some degree the impurities sought to be removed. A useful solvent is an alkanol, such as methanol. However, it is most preferred to wash the bisimide product with a wash solvent mixture containing a nonpolar constituent, such as an aromatic hydrocarbon or halohydrocarbon, and an organic acid. The nonpolar and organic acid constituents of the wash solvent can be, respectively, any of the aromatic hydrocarbons or halohydrocarbons and any of the organic acids before described for the constituents of the solvent used in the process of this invention. It is most preferred to use the same wash solvent constituents which were used to prepare the bisimide product since such eliminates the need for separation between the reaction filtrate and the wash filtrate. A preferred wash solvent is one comprised of xylene and propionic acid in the same proportions as that used for the xylene and propionic reaction solvent before described. Use of the preferred wash solvent yields a bisimide product having a very low acid number. This is a surprising result in view of the presence in the solvent of the organic acid constituent.

If the electrical conductivity of the formulation in which the bisimide product is to be a part is of no concern, it is possible to lower the acid number even further by adding about 0.5 to about 2.0 weight percent alkali metal acetate salt to the reaction mass, the weight percent being based upon the amount of tetrabromophthalic anhydride used to form the reaction mass. It is convenient to provide the acetate salt with the anhydride charge to the reaction vessel. Preferred acetate salts are potassium acetate and sodium acetate.

When washing the bisimide product, at least one void volume of the wash solvent should be used. Typically, from about 75 percent to about 85 percent of the cake volume is void volume. (A void volume is defined as that volume of the bisimide product to be washed which is not occupied by bisimide product particles. Preferably, the wash volume is 2 to 3 times the void value. The wash temperature can vary from 0° C. to 150° C. depending upon the vapor pressure of the solvents and the equipment limitations. In general, the higher the temperature of the wash, the shorter the wash time. For most solvent systems, the optimum wash temperature is dependent upon the temperature tolerance of the filter media used. Further washing with water or an alcohol is not necessary and, from a process economy viewpoint, not desirable.

After washing, the washed bisimide product is dried conventionally, say for a period of from about 12 to about 48 hours at a temperature of from about 125° C. to about 140° C.

The bisimide product produced by the process of this invention not only has good thermal stability and resistance to UV degradation, but also has a low acid number, less than about 1.0, and a high bromine content, i.e. within the range of from about 60 percent to about 67 percent. Washing with the preferred wash solvent can give a bisimide product having an acid number as low as 0.05.

The bisimide product of this invention may be used as a flame retardant in formulation with virtually any flammable material. The material may be macromolecular, for example, a cellulosic material or a polymer. Illustrative polymers are: olefin polymers, cross-linked, and otherwise, for example, homopolymers of ethylene, propylene, and butylene; copolymers of two or more of such alkylene monomers, and copolymers of one or more of such alkylene monomers, and any other copolymerizable monomers, for example, ethylene/propylene copolymers, ethylene/ethyl acrylate copolymers, and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyl resins; phenolics; elastomers, for example, butadiene/styrene copolymers and butadiene/acrylonitrile copolymers; terpolymers of acrylonitrile, butadiene, and styrene; natural rubber; butyl rubber; and polysiloxanes. The polymer may also be a blend of various polymers. Further, the polymer may be, where appropriate, cross-linked by chemical means or by irradiation.

The amount of bisimide product used in a formulation will be that quantity needed to obtain the flame retardancy sought. It will be apparent to those skilled in the art that for all cases no single precise value for the proportion of the bisimide product in the formulation can be given, since this proportion will vary with the particular flammable material, the presence of other additives, and the degree of flame retardancy sought for in any given application. Further, the proportion necessary to achieve a given flame retardancy in a particular formulation will depend upon the shape of the article into which the formulation is to be made, for example, electrical insulation, tubing, and film will each behave differently. In general, however, the formulation may contain from about 3 to about 40 weight percent, preferably 10 to 30 weight percent, of the bisimide product when it is the only flame retardant compound in the formulation. The weight percent amounts are based upon the total weight of the formulation.

It is especially advantageous to use the bisimide product of this invention and an inorganic compound, especially the oxide, of a Group V element, for example, bismuth, arsenic, phosphorus, and especially antimony, in the formulation. Of these compounds, antimony oxide is especially preferred. If such a compound is present in the formulation, the quantity of bisimide product needed to achieve a given flame-retardancy is reduced.

Formulations containing a bisimide product/inorganic compound flame retardant system may contain up to about 40% by weight of the system, preferably between 10 and 30% by weight.

It is believed that the bisimide product and the inorganic compound will react under the conditions of combustion of a flammable material to form inorganic bromine compounds, e.g., hydrogen bromide and oxybromides, which assist in retarding combustion. The bromine-bearing bisimide product also acts as a flame retardant independently, and the proportions of the bisimide product and inorganic compound in a flame retardant system are a matter of choice, depending on the material in which the system is to be incorporated and commercial considerations. Generally, the bisimide product and the inorganic compound are in a weight ratio of from about 1:1 to about 7:1, and preferably of from about 2:1 to about 4:1.

The formulations containing the bisimide product of this invention may contain any of the additives usually present in such formulations, e.g. glass fibers, plasticizers, nucleating agents, antioxidants, filler, pigment, UV stabilizers, etc.

The inventions disclosed herein are illustrated by the following non-limiting Examples.

EXAMPLE I

To a glass-lined reactor which was jacketed for heating and cooling, and which was equipped with an agitator and a glass-lined overhead reflux system was charged 10,800 pounds of a mixed solvent which was approximately 27 weight percent propionic acid and 73 weight percent commercial grade mixed xylenes. The reactor jacket was used to heat the reactor contents to about 90° C. and then 5100 pounds of tetrabromophthalic anhydride were added to the reactor. The reactor contents were then heated under nitrogen pressure to 165° C. and then the pressure controlled at about 20 psig to achieve reflux of the contents. When the reactor temperature stabilized at 165° C., a mixture of 331.3 pounds of ethylene diamine and 566.7 pounds of commercial grade mixed xylenes was fed to the reactor over a period of 4.6 hours. During this feed period, the reaction mass was at reflux and the reactor pressure was maintained constant at 20 psig but the reactor temperature dropped below 165° C. due to the formation of water as a result of the reaction. When the reactor contents reached a temperature of about 140° C., a stream comprised of water and small amounts of propionic acid was removed from the reflux stream by means of a phase separator so as to maintain the reactor temperature at about 140° C. After the feed period was completed, the reactor was maintained at about 140° C. for an additional 5 hours. This 5 hour period represented the cook period. During the cook period the reaction mass was at reflux. At the end of the fifth hour of the cook period, water withdrawal from the reflux stream was again started to raise the reactor temperature to about 160° C. The total aqueous stream removed during the entirety of the process was measured to be 534 pounds. The reactor contents were cooled to 80° C. by shutting off the heat source to the jacket and then using depressurization and vacuum to accomplish evaporative cooling. During the evaporative cooling approximately 3000 pounds of the reaction solvent was withdrawn from the reflux stream to increase the reaction slurry solids concentration from 30 weight percent to 40 weight percent. The reactor contents were fed to a 48 inch by 30 inch perforated basket centrifuge and the solids were separated from the remainder of the reactor contents. The product was wet and in cake form. This product was washed with a mixture containing 30 weight percent propionic acid and 70 weight percent xylene that had been obtained by distillation from the centrifugates of previous batches. The wash temperature was 80° C. The washed wet cake was then dried in a rotating vacuum drier at a pressure of 125 to 300 mm Hg absolute and a temperature of 140° C. The quantity of dry product recovered was 4,946 pounds, representing a yield of 94.6 percent based on the quantity of tetrabromophthalic anhydride originally charged to the reactor. The N,N'-ethylene-bis(tetrabromophthalimide) predominant product gave the characteristics shown below:

| | |
|---|---|
| Initial Melting Point | 456.0° C. |
| Loss on Drying, 180° C. - Full vacuum, 1 hour | 0.16 wt % |
| Acid Number, mg KOH/g | 0.49 |
| Particle Size, microns | |
| Average | 3.6 |
| 99% less than | 12.0 |
| Hunter Colorimeter Values | |
| L | 90.3 |
| a | −1.24 |
| b | 3.5 |
| Y.I. | 6.3 |

What is claimed:

1. A process for preparing a bisimide product which principally contains a bisimide of the formula,

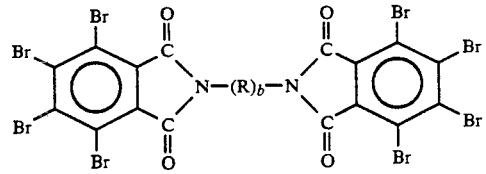

wherein R is an alkylene radical containing 1 to 6 carbon atoms and b is 1 or 0, said process comprising:
(a) providing, in a reaction vessel, a solution containing tetrabromophthalic anhydride and a solvent, which solvent contains at least about 15 weight percent of a mono-, di- or tri- carboxylic acid having a dissociation constant not higher than $1.0 \times 10^{-3}$ at 25° C.,
(b) forming, at a temperature within the range of from about 140° C. to about 200° C., a reaction mass by adding to said solution a diamine of the formula,

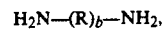

a diamine salt formed by the partial or total diamine neutralization of a mono-, di- or tri- carboxylic acid having a dissociation constant not higher than $1.0 \times 10^{-3}$ at 25° C. or a mixture of said diamine and said diamine salt, said formation of said reaction mass resulting in the production of a bisimide precipitate which becomes a constituent of the reaction mass;
(c) during the formation of the reaction mass;
(i) maintaining a substantial constant pressure in the reaction vessel, and
(ii) removing, from the reaction mass, that amount of water formed during the formation which is necessary to keep the reaction temperature from falling to a temperature below about 140° C., (d) terminating said addition of said diamine or diamine salt when the molar ratio of said tetrabromphthalic anhydride initially present in said solution to said diamine or diamine salt added is within the range of from about 1.9:1 to 2.1:1;

(e) recovering, as said bisimide product, the produced bisimide precipitate.

2. The process of claim 1 wherein said solvent comprises propionic acid and o-, m-, p- xylene or mixtures of such xylenes.

3. The process of claim 2 wherein said propionic acid is present in an amount within the range of from about 15 to about 30 weight percent.

4. The process of claim 1 wherein R is an ethylene radical and b is 1.

5. The process of claim 1, wherein the amount of water removed (c)(ii) does not exceed 75% of the water formed during the formation of the reaction mass.

6. The process of claim 1 wherein said temperature during the formation of said reaction mass does not exceed about 170° C. and does not fall below 140° C.

7. The process of claim 3 wherein said temperature during the formation of said reaction mass does not exceed about 170° C. and does not fall below 142° C.

8. The process of claim 3, wherein the amount of water removed (c)(ii) does not exceed 75% of the water formed during the formation of the reaction mass.

* * * * *